(12) United States Patent
Viherlahti

(10) Patent No.: US 8,955,777 B2
(45) Date of Patent: Feb. 17, 2015

(54) METHOD FOR PRODUCING SALT DUST AND SALT DUST GENERATOR

(76) Inventor: Kari Viherlahti, Nummela (FI)

( * ) Notice: Subject to any disclaimer, the term of this patent is extended or adjusted under 35 U.S.C. 154(b) by 549 days.

(21) Appl. No.: 13/302,216

(22) Filed: Nov. 22, 2011

(65) Prior Publication Data

US 2012/0126043 A1    May 24, 2012

(30) Foreign Application Priority Data

Nov. 24, 2010    (FI) ...................................... 20100393

(51) Int. Cl.
*B02C 19/06*    (2006.01)
*A61K 9/00*    (2006.01)
*A61M 11/02*    (2006.01)

(52) U.S. Cl.
CPC .............. *A61K 9/0075* (2013.01); *A61M 11/02* (2013.01)
USPC ................................................ 241/5; 241/40

(58) Field of Classification Search
USPC .................................................. 241/5, 39, 40
See application file for complete search history.

(56) References Cited

U.S. PATENT DOCUMENTS

| 3,312,342 | A | * | 4/1967 | Brown | ............................... 209/3 |
| 3,362,405 | A | * | 1/1968 | Hazel | ....................... 128/203.15 |
| 7,086,619 | B2 | * | 8/2006 | Hefle et al. | ....................... 241/40 |

FOREIGN PATENT DOCUMENTS

WO    2008/060173 A1    5/2008

* cited by examiner

*Primary Examiner* — Mark Rosenbaum
(74) *Attorney, Agent, or Firm* — Ziegler IP Law Group, LLC

(57) ABSTRACT

A salt dust generator and method for producing salt dust that is used in salt therapy are described where salt dust is generated when salt particles that are moved in an air flow collide with each other and with certain parts of a salt dust generator. By regulating the speed of the air flow, thus changing its capability to carry the salt particles, and using obstacles, for instance nets that are placed into the salt dust generator vessel, it is possible to increase the amount of the collisions of the salt particles and thus make the formation of the salt dust more efficient.

6 Claims, 2 Drawing Sheets

METHOD FOR PRODUCING SALT DUST AND SALT DUST GENERATOR

BACKGROUND

1. Field

The present disclosure relates to salt therapy systems, and in particular to a method for producing fine salt dust in the breathing air by means of a device producing salt dust, i.e. salt dust generator—and the salt dust generator used in the present method.

2. Brief Description of Related Developments

The method and the generator in accordance with aspects of the disclosed embodiments are used for example in salt room therapy, wherein fine salt dust is blown by a salt dust generator into a room lined with salt. The salt dust provides the room air with negatively charged particles that, when inhaled, have infection reducing and phlegm detaching influence in the respiratory tract, thus opening the tract and easing respiration. In salt room therapy, the amount of salt that reaches the body system is so small that it does not cause additional swelling or adverse increase in blood pressure. Typically, a treatment session takes about 40 minutes at a time for an adult and about 5-10 minutes for a small child.

Currently, on the occasions described above, a method is used wherein the salt generator automatically measures out the right amount of granular salt into a steel tank, wherein blades operated by a motor consequently mill the salt fine. The salt dust thus provided is thereafter conducted by air flow into the air of the salt room to be inhaled by the patient. Salt particles are known to have a therapeutic effect when their size is less than 5 micrometers.

Another method to produce fine salt dust is to blow air thought a vessel where the lid and the bottom are made of net. The salt particles that have been put into the vessel fly in the air flow, collide with each other and break down to smaller particles. In this method, it is also possible to use obstacles inside the vessel such as, for example, nets to increase the amount of collisions. When the salt particles that have passed the obstacles come to the other end of the vessel, a part of them has reached a smaller size that is favourable for the health, i.e. the particles are less than 5 micrometers in size.

The main disadvantage of the current techniques can be considered to be that a great proportion of the salt particles produced are larger than 5 micrometers in size, rendering them useless for purposes of the therapy. Thus, a reasonable effort will not provide an optimal result with regard to the particle size of the salt.

The prior-art technique described above is widely employed in salt room therapy and salt mask therapy. One method and apparatus to produce fine salt dust is presented in the patent publication no: WO 2008/060173. The apparatus according to this publication has a vessel, wherein the salt material to be made fine is put, and it also includes a filter that has been put inside the vessel between two nets. When the air is blown into the vessel through a hole in its bottom, the salt particles collide with each other and then they penetrate through the filter. A part of the salt particles that are lead to the mask are favourably less than 5 micrograms in size. It is evident that the size of the filter in this prior-art technique cannot be set so that only the particles of max 5 micrometers of size can penetrate through it because this would cause the filter to clog very soon. In this case, one must be satisfied with an end result where only a part of the particles going to the therapy are less than 5 micrometers in size.

Accordingly, it would be desirable to provide a salt room therapy system and device that addresses at least some of the problems identified above.

SUMMARY

As described herein, the exemplary embodiments overcome one or more of the above or other disadvantages known in the art.

The aspects of the disclosed embodiments are directed to a method and apparatus that overcomes the disadvantages of the prior-art techniques.

The salt particles generated by the method according to the disclosed embodiments are therapeutically useful, less than 5 micrometers in size. Therefore, the therapy provided by the method is safer and can be targeted more accurately than that with prior-art techniques. As an example of advantages obtained by using the method according to the present disclosure, it can be mentioned that salt dust that is dry and fine enough also penetrates efficiently into the periphery of the respiratory tract. Also, when entering the skin pores, the salt dust absorbs moisture from the surrounding air even better than before and thus keeps the skin moisturised and elastic.

An indisputable advantage is achieved also with a salt dust generator incorporating aspects of the disclosed embodiments because of its construction and operation principle. The milling of the salt particles in it is based in a simple mechanical procedure and the separation of the particles that are suitable for the therapy from the rest of the particles is based in physical event. Therefore, the apparatus according to the aspects of the disclosed embodiments has a simple construction and is easy to manufacture. This, in turn, is advantageous economically.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and unless otherwise indicated, they are merely intended to conceptually illustrate the structures and procedures described herein. In addition, any suitable size, shape or type of elements or materials could be used.

BRIEF DESCRIPTION OF THE DRAWINGS

The aspects of the disclosed embodiments will be described in more detail by the attached drawings, wherein.

DETAILED DESCRIPTION OF THE DISCLOSED EMBODIMENTS

Below, exemplary embodiments of the disclosure will be described by way of an example of its structure and function, with reference to the above mentioned figures.

Figure 1:
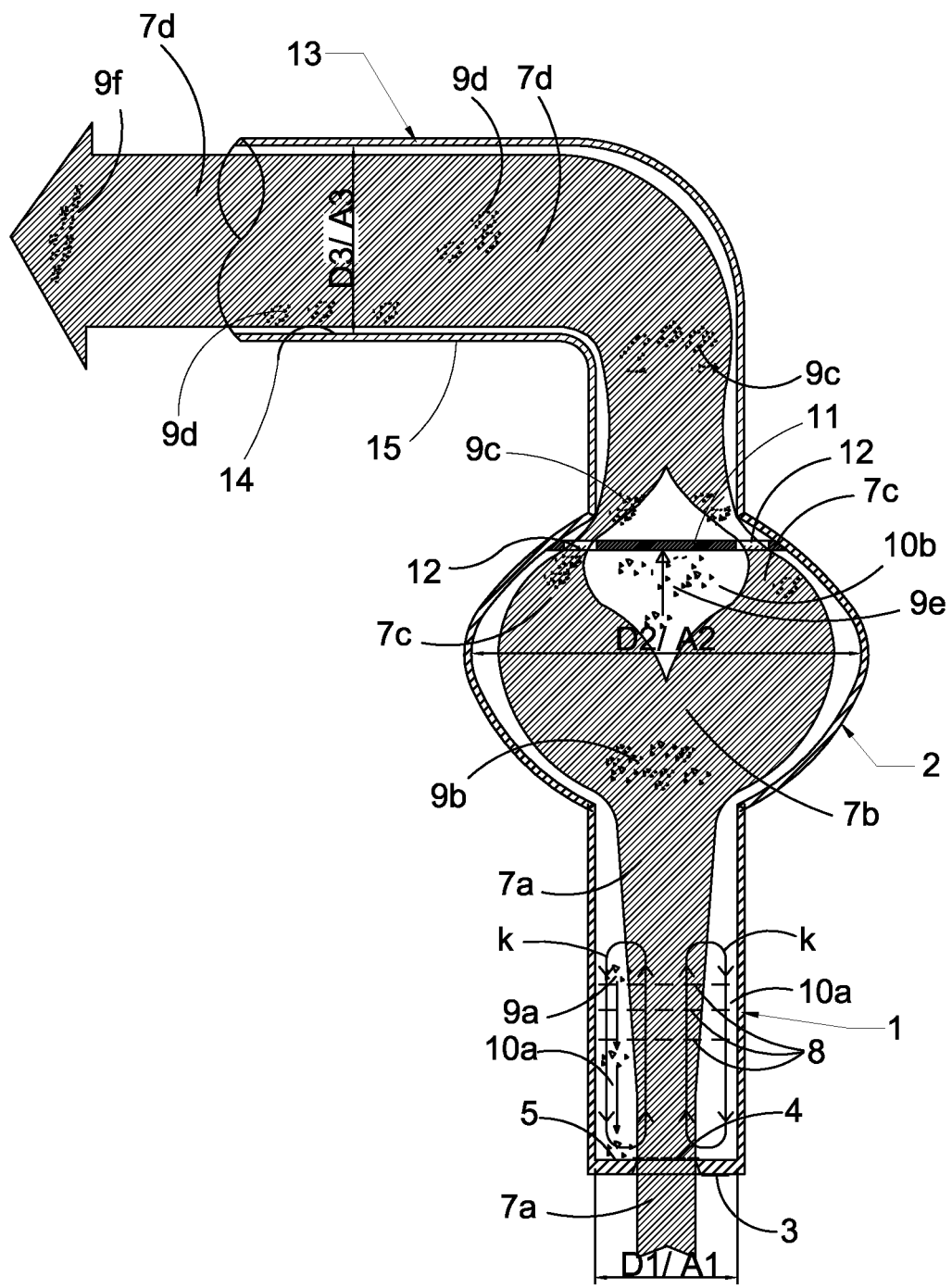
FIG. 1 shows a vertical section of the schematic view of the salt dust generator according to an aspect of the disclosed embodiments in operational readiness.
Figure 2:
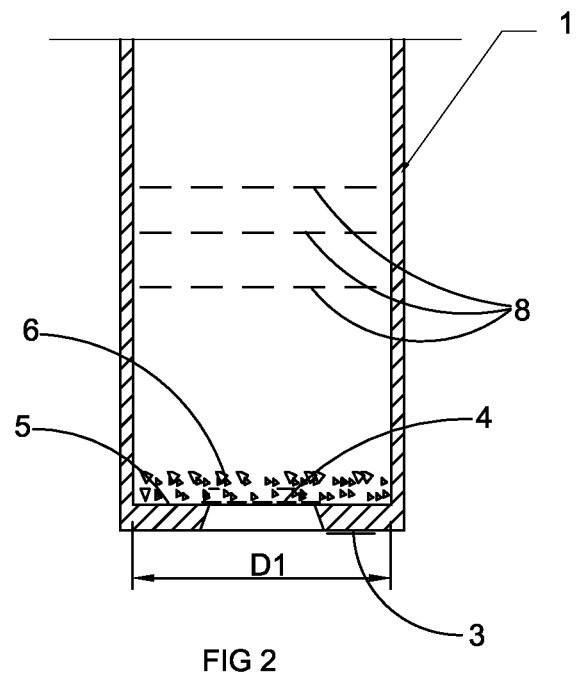
FIG. 2 shows a vessel lower part section of the schematic view of the salt dust generator according to an aspect of the disclosed embodiments.
Figure 3:
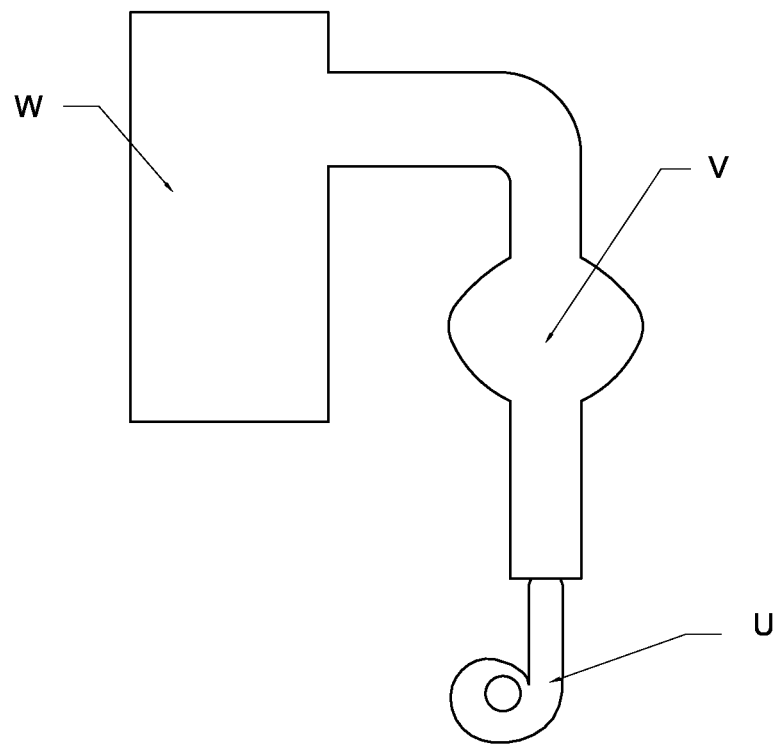
FIG. 3 shows a schematic view of the apparatus used in the salt dust generator according to an aspect of the disclosed embodiments.

The salt dust generator, in one embodiment, is formed by a vessel 1 (FIG. 1) with a cylindrical shape standing in an upright position, preferably about 300 mm in height and the diameter D1 about 80 mm. Upon this vessel 1, there is a flow space 2 which in this example is essentially of the shape of an egg, the greatest diameter being about 250 mm. The bottom 3 of the vessel 1 is partially net. The net 4 is in the middle of the bottom covering about a half of the surface A1 of the bottom 3 diameter D1. The material is solid in the peripheries of the bottom forming a ring like area 5. A layer of about 20 mm of granular salt 6 is placed upon the bottom 3 (FIG. 2). The salt particles are bigger than the mesh size of the middle part net 4 of the bottom 3 so that they remain inside the vessel 1. Air 7a is blown through the net 4 of the bottom using a fan and thus the salt particles start moving. While moving, the salt particles collide with each other and with the collision obstacles that have been installed inside the vessel 1 in its lower part, i.e. against nets 8, and thus the size of the particles decreases and the amount of them increases. As the peripheral area 5 of the bottom 3 is solid the air flow 7a goes only through the net in the middle leaving the peripheral area 10a outside of the air flow. When the air flow 7a is regulated suitable, the biggest of the flying salt particles 9a fall back to the bottom when they come to this area of weaker air flow 10a. Due to the pressure difference between the stronger and weaker air flow, these particles get sucked back to the stronger air flow 7a and they rise again and collide again with each other and the nets 8. When the salt particles that have been ground and broken smaller and the salt particles that are bigger and capable of going up 9b in the air flow 7a in the middle of the vessel 1, when they get to the flow space 2 upon the vessel 1, the cross-sectional area gets bigger when going to the direction of the air flow, that is upwards, and the speed of the air flow 7b degreases and it is no more capable of keeping the heaviest salt particles flying, they start falling downwards. A part of the middle size salt particles that are not yet suitable for the salt therapy continue their way upwards and they collide with the plate 11 in the upper part of the flow space 2 because their weight is too much for being able to change the direction of flow according to the air flow 7c and thus pass the plate 11 through the openings 12 in its peripheral area. The total area of these openings 12 is favourably smaller than the area A3 corresponding the diameter D3 in the horizontal part 15 of the tube 13 that will be presented later in more detail. The salt particles 9c that are small enough in this phase of the process change direction with the air flow 7c and escape the flow space 2 through the openings 12. They go further to the tube 13 and the cross-sectional area of the horizontal part 15 is greater than the total area of the openings 12 and the cross-sectional area of the vertical part of the tube 13. Due to the difference of the before mentioned areas, the speed of the air flow 7d decreases when coming to the horizontal part 15 of the tube 13 and its power is not sufficient to carry further in the tube those salt particles 9c that are in size unfavourable for the therapy, over 5 micrometers. These salt particles 9d fall to the bottom 14 of horizontal part 15 of the tube 13. When the circulation of the salt particles in the vessel 1 down part peripheral area 10a has lasted sufficiently long time and the amount of collisions of the salt particles is sufficient, all the salt particles have become so light that they can move to the flow space 2 with the air flow 7a. When the salt particles 9e that have come to the flow space 2 but are not yet capable of changing direction with the air flow 7c, have collided a sufficiently long time with the plate 11 in the flow free space 10b they become capable of this change of direction and they escape from the flow space 2 through the openings 12. The salt dust 9f that flies in the air flow 7d is directed to the therapy device W, like salt mask, salt tent or salt room. The grain size of this salt dust 9f is almost completely less than 5 micrometers.

In alternate embodiments, the vessel 1, the flow space 2 and the shape of the tube 13 of the salt dust generator can also be something else than what is described in the above mentioned example. These features can be selected in respective cases according to the prevailing situation. The vertical part of the tube 13 can be made of a flexible material in which case the mutual position of the therapy device W, like a salt mask, and the salt dust generator can vary in certain limits. It is essential to arrange the velocities of the air flows in the different parts of the apparatus and the mutual speed differences favourable so that salt particles colliding with each other get fine and the capacity of the air to carry particles causes separation of particles with the end result that only the particles that are almost all less than 5 micrometers come to the therapy.

Likewise the amount of salt that is used can vary and be dependent on the before mentioned capabilities of the salt dust generator. The size of the salt grains that are used does not limit the usage range of the method or the salt dust generator, but on the contrary, the method and the apparatus can be set to operate always according to the salt grain size in use.

The salt particles 9*d* that land on the bottom 14 of the horizontal part 15 of the tube 13 are removed from the tube sufficiently often during maintenance shutdown periods. The bottom 14 of the tube 13 can be formed so that these salt particles 9*d* gather in certain places, like for instance into a hollow that has been made to the bottom 14 of the tube 13 for these particles. The removal of the salt particles 9*d* can be made for instance by disconnecting the salt dust generator from the therapy device W.

The relation of the solid periphery area 5 with the bottom netlike area 4 of the vessel 1 of the salt dust generator in accordance with aspects of the disclosed embodiments can be any suitable relation.

In a further embodiment, the salt dust generator can also be made without the inside net 8 of the vessel 1 and in that case the salt dust 9*f* is obtained by the collision of the salt particles with each other and by the collision of the salt particles with the plate 11 of the vessel 1.

The parts of the salt dust generator can also be positioned differently than in the above example. Any position of the vessel 1, flow space 2 and pipe 13 can be considered if they are favourable for the production of the salt dust 9*f* within the frames of the aspects of the disclosed embodiments as stated in the claims.

The salt dust generator can be made of any material that is suitable for its purpose. One favourable material for the vessel 1, flow space 2 and the horizontal part 15 of the pipe 13 is glass and then it would be easy to see the formation of the salt dust 9*f*.

It must be noted that although this explanation pertains to a certain type of favourable application of the disclosed embodiments, it is not the intention to limit in any way the use of the present disclosure to only this type of example but many variations are possible within the inventive idea of the present disclosure as stated herein and in the claims. Moreover, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for producing fine salt dust in the breathing air by a salt dust generator comprising:
   providing granular salt particle in a bottom of the salt dust generator,
   providing an air flow through a net disposed in an opening in the bottom of the salt dust generator, a direction of the air flow going-upwards from the bottom of the salt dust generator through a flow space region and into a tube section, the air flow causing
      the salt particles in the bottom of the salt dust generator to travel upwards and collide with each other and at least one wall of the salt dust generator,
   changing a cross-sectional area of a flow space in the salt dust generator in the flow space region in the direction of the air flow, to decrease a speed of the air flow until a carrying capability of the air flow is not sufficient to lift heavier salt particles in the flow space and wherein the heavier salt particles fall back towards the bottom of the salt dust generator,
   regulating a power of the air flow so that when the salt particles fly in the air they rise to the flow space and that the salt particles in periphery area of the bottom of the salt dust generator around the opening are moved into the air flow,
   providing a plate in an upper region of the flow space and regulating the air flow to cause heavier particles in the air flow to collide with the plate, while lighter particles in the air flow escape the flow space through holes in a periphery of the plate, the upper region of the flow space being narrower than a middle region,
   decreasing a speed of the air flow in the tube so that the lighter particles entering the tube through the holes in the periphery of the plate so that salt particles that have a size greater than approximately 5 micrometers fall to a bottom of the tube, the tube being substantially horizontally oriented relative to the flow space region of the salt dust generator.

2. The method of claim 1, further comprising providing the salt dust having a size of less than approximately 5 micrometers from the tube to a therapy device.

3. The method of claim 1, comprising cause the salt particles in the flow space to collide with the plate, each other and the walls of the salt dust generator until the salt particles in the flow space are of a sufficient size and weight to travel through the openings in the periphery of the plate and into the tube.

4. The method of claim 1, comprising changing the cross-sectional area of the flow space in the direction of the air flow from a first cross-section to a second cross-section, an area of the first cross-section being smaller than an area of the second, and from the second cross-section to a third cross-section, an area of the third cross-section being smaller than the area of the second.

5. The method of claim 1, comprising providing an area of the opening in the bottom of the vessel comprises substantially in the range of $1/10$ to $8/10$ of a total area of the bottom.

6. The method of claim 1, comprising
   the net having a mesh size; and
   providing salt particles bigger than the mesh size.

* * * * *